United States Patent [19]

Abraham

[11] Patent Number: 5,854,284

[45] Date of Patent: Dec. 29, 1998

[54] CANDLE FOR DISPERSION OF INSECT REPELLENT BASED ON DEET

[76] Inventor: Carl J. Abraham, 3 Baker Hill Rd., Great Neck, N.Y. 11023

[21] Appl. No.: 984,843

[22] Filed: Dec. 4, 1997

Related U.S. Application Data

[63] Continuation-in-part of Ser. No. 803,803, Feb. 24, 1997, Pat. No. 5,738,862, which is a continuation of Ser. No. 769,993, Dec. 19, 1996, abandoned.

[51] Int. Cl.$^6$ .......................... A61K 35/78; A61K 31/045; A01N 9/02; A01N 9/20

[52] U.S. Cl. .......................... 514/511; 514/532; 514/544; 514/552; 514/617; 424/40; 424/403; 424/411; 431/288

[58] Field of Search ...................... 514/511, 532, 514/544, 552, 617; 424/40, 403, 411; 431/288

[56] References Cited

U.S. PATENT DOCUMENTS 3,898,039  8/1975  Lin ............................................. 21/55

*Primary Examiner*—Frederick Krass
*Attorney, Agent, or Firm*—Levine & Mandelbaum

[57] ABSTRACT

An insect repellent candle including a liquid containing DEET and a fragrance oil which acts as a carrier for dispersing DEET vapor into the atmosphere upon evaporation of the fragrance oil. The liquid system is contained within the wax of a candle which can be burned to emit DEET vapor into the atmosphere.

6 Claims, No Drawings

CANDLE FOR DISPERSION OF INSECT REPELLENT BASED ON DEET

This application is a continuation-in-part of my U.S. patent application Ser. No. 08/803,803 filed Feb. 24, 1997, now U.S. Pat. No. 5,738,862 issued Apr. 14, 1998, which is a continuation-in-part of my U.S. patent application Ser. No. 08/769,993 filed Dec. 19, 1996, now abandoned.

BACKGROUND OF THE INVENTION

This invention relates to insect repellents based on N, N-diethyl-m-toluamide, commonly referred to as "DEET". More specifically, the invention is directed to the incorporation of DEET into a solid or liquid medium, i.e., a candle, from which the DEET, a liquid of extremely low volatility, can vaporize at ambient temperatures at a rate sufficient to repel insects, and at greater rates when a candle containing my deet formulation is lit to heat the candle wax and the deet and oil composition which it contains.

It is known to use DEET in the prior art to repel insects from a surface by depositing liquid DEET on the surface. However, prior to the instant invention, the use of DEET as a vapor to repel insects without requiring contact of the insects with a surface containing DEET was not known.

Various prior art products seek to repel insects from human beings with limited success. One commercially available topical application works for a very short period of time, i.e. on the order of 10–20 minutes, or even substantially less if the wearer perspires.

There are repellent devices in the prior art that emit high frequency sounds to repel insects. The female mosquito which is a major factor in bites is deaf and undeterred by such devices. Nor are audible energy devices very effective against other insects. There are also devices that can be plugged into a standard A.C. wall outlet to emit insect repelling substance in response to application of the voltage. These devices are intended to kill, not merely repel, insects and are toxic.

It is also known in the prior art to encapsulate insect repellents in time control release agents. Examples of such repellent systems are disclosed in U.S. Pat. Nos. 4,548,764 to Munteanu et al. and 5,069,231 to Rutherford. Prior art repellent encapsulation systems have a very limited life and are typically effective for less than one week. Such prior art systems are also very complex in that they require lactone groups and hydroxyl groups, and/or polyurethane in the repellent medium. Others call for polyoxyalkylene diols, linear polyster diols, and the reaction product of one or more alkylene diols with a difunctional linear polyester derived from the condensation of one or more diols with one or more dibasic acids. Still others require poly(epsilon caprolactone) as a cross linking agent for polyurethane. Highly volatile materials such as esthers, ethers, and aldehydes are commonly found in prior art compositions. Such prior art compositions are inherently unstable and therefore require stabilizers.

The prior art has, until now, failed to provide a molded system created without encapsulation that results in the slow vaporization of a relatively non-volatile liquid into the air to repel flying insects.

It is also known in the prior art to use citronella candles to repel insects. However, tests of shown that citronella is not a very effective insect repellent even when released into the air from a candle. Recent studies have shown that the long held perception that citronella is an effective insect repellent is based on a myth.

Air-wick systems have bean used in the prior art to refresh air with a fragrant odor. However, none has been used in conjunction with a relatively non-volatile insect repallant liquid such as DEET to create a repellent vapor in the air surrounding the system.

SUMMARY OF THE INVENTION

The aforementioned problems of the prior art are overcome by the instant invention which provides for the incorporation of a mixture of DEET and a fragrance oil into the wax of a candle. When the candle is lit, the DEET withstands the heat of the candle and is carried into the atmosphere with the vaporized fragrance oil and candle wax to form an effective system for repelling insects through the emission of DEET vapor therefrom and its dispersion into the atmosphere.

The invention, for the first time, enables the use of DEET vapor as an insect repellent through the use of fragrances containing middle and low note ingredients that, during molding into products, retain large amounts of residual ingredients and short term exposures to 170° F. to 195° F. The Deet formulation may also be applied to limited areas of the body by dabbing a towelette containing the Deet solution of the invention onto limited areas of the body, e.g., the wrists and elbows. Because the Deet is dispersed into the surrounding air, such limited applications are effective in repelling insects before this reach the body thereby rendering the entire body protected.

It is therefore an object of the invention to provide an insect repellent medium from which DEET vapor can be dispersed at ambient temperatures to repel insects.

Another object of the invention is to provide an insect repellent medium from which DEET vapor can be dispersed from a solid or liquid medium over a life on the order of a month or more.

Still another object of the invention is to provide an insect repellent medium which is effective in repelling insects yet non-toxic to humans and animals.

A further object of the invention is to provide an insect repellent medium from which utilitarian products such as bracelets and tablecloths can be fabricated.

Other and further objects of the invention will be apparent from the following description of a preferred embodiment of the invention.

DESCRIPTION OF THE PREFERRED EMBODIMENT

The present invention employs a mixture of DEET and a volatile fragrance oil having residual ingredients that are retentive, preferably in the range of 170° F.–195° F. The DEET and fragrance oil are incorporated into a thermoplastic system such as polyethylene or polystyrene in conjunction with copolymers to form a solid product which can be molded at elevated temperatures to form utilitarian products having insect repellent qualities. The intertwining of polymeric domains results in an association complex with DEET and fragrance ingredients in a liquid state contained within the thermoplastic system. The DEET rises to the surface of the thermoplastic material and, with the fragrance components retained after molding, is vaporized thereby enabling it to repel insects without requiring contact of the insects with a surface on which the DEET is deposited.

Insect repellent wrist bracelets and tablecloths have been fabricated in accordance with the invention as have candles which can be burnt to release DEET vapor into the atmosphere to repel insects. Alternatively, the liquid system formed from the solution of fragrance oil and DEET can be or placed in a solution of alcohol or water and alcohol and dispersed through capillary action in a wick system and evaporation of the fragrance oil and DEET vapor into the atmosphere.

DEET is a nonvolatile liquid at room temperature and has a boiling point of approximately 320 degrees F. Hence it is inherently unsuitable as an insect repellent unless dispersed into the atmosphere by a carrier system or applied directly to the skin by liquid spray or liquid applicators. Thermogravametric analysis on a solid composition containing DEET in accordance with the invention confirms that DEET is vaporized and dispersed into the atmosphere with a suitably formulated fragrance oil at approximately 170–195 degrees Fahrenheit. That is, it has now been discovered that notwithstanding its high boiling point, DEET vapor can be dispersed into the atmosphere by a carrier consisting of a formulated fragrance oil having a lower boiling point.

A thermoplastic system including polyethylene or polystyrene in conjunction with copolymers melts in the range of 150 degrees F. to 225 degrees F. In accordance with the invention, a thermoplastic system containing a fragrance oil carrier and DEET as an active ingredient for repelling insects, is molded in a closed, i.e., air-tight, system to minimize escape of the volatile constituents. Molding is done at a nominal temperature range of 180 degrees F. to 200 degrees F. in the closed system. By overloading the thermoplastic system in its liquid form with DEET in the closed system up to 20 percent of the DEET and fragrance can be retained in the molded product.

Until the invention, the use of DEET as an insect repellent for people has required application by liquid or spray to the epidermis of the person. Never in the prior art has a vapor of DEET emitted from a carrier not applied to the skin been used as the repellent. Applicant has discovered that only a very small amount of DEET vapor is necessary to repel flying insects including, without limitation, mosquitoes flies, gnats, flees and bees.

The invention is also based, in part, on the discovery of a volatile material that is compatible with DEET. The volatile material is mixed with DEET to form an insect repellent solution. It has been found that a fragrance oil that has a large amount of residual ingredients at short term exposures to 170° F.–195° F. is a volatile material which can carry molecules of DEET vapor into the atmosphere where they are dispersed and act as a repellent against flying insects.

Advantageously, the liquid system formed from the solution of suitably formulated fragrance oil and DEET can be molded into solid plastic pellets which can then be molded into utilitarian objects, e.g., wristbands and tablecloths, capable of repelling insects can be fabricated by conventional methods. The liquid system formed from the solution of fragrance oil and DEET can be mixed into a wax from which candles are molded. Also, the liquid system formed from the solution of fragrance oil and DEET can be or placed in a solution of alcohol or water/alcohol in conjunction with a wick system to disperse the DEET vapor into the atmosphere in order to repel insects from a specific locale as a result of a timed vapor release system. The same solution can be applied to towelettes, i.e., small disposable towels, which can then be used as applicators to apply the Deet based repellent solution to areas of the body of a person, for example, the wrists and elbows, from which the Deet can be dispersed into the local atmosphere to repel insects from the region surrounding person, again due to the timed vapor release system.

In a first embodiment of the invention an insect repellant system is created by a mixing a liquid system containing a suitably formulated volatile fragrance oil and DEET and imbedding the liquid system within a thermoplastic resin system. In order to prevent flashing off of the volatile fragrance oil during the molding process, a thermoplastic system that can be molded at temperatures under 200° F. (93° C.) must be used.

Many fragrance oils are incapable of withstanding the temperatures a molding process, even at the aforementioned relatively low molding temperatures. It is therefore important to select a fragrance oil which does not have substantial amounts of low volatile ingredients, i.e., top notes, that would flash off during the molding process. The fragrance oil into in which the DEET is mixed to form the liquid system employed in the invention must contain ingredients that can retain the intended odor or fragrance, after subjection to molding temperatures ranging between 180° F. and 200° F. (82.2° C.–93.3° C.) for periods of up to approximately 15 seconds.

It is been found that the polymeric thermoplastic system into which the solution of DEET and fragrance oil is incorporated during molding can include polyethylene in an amount ranging from 80% to 90% by weight and ethylene vinyl acetate (EVA) co-polymer in an amount ranging from 10% to 20% by weight, with a combination melt index of 24. In the preferred embodiment of the invention, the thermoplastic system includes 90% polyethylene and 10% ethylene vinyl acetate (EVA) co-polymer by weight. Alternatively, the polymeric thermoplastic system into which the solution of DEET and fragrance oil is incorporated during molding can include polyethylene in an amount ranging from 70% to 90% by weight and ethylene-n butyl acrylate copolymer in an amount ranging from 10% to 30% by weight. In the preferred embodiment of the invention, the thermoplastic system includes polyethylene in an amount 80% by weight and ethylene-n butyl acrylate copolymer in an amount 20% by weight.

A fragrance oil suitable for mixing with DEET and having the characteristics of sufficiently low volatility to prevent excessive flash off during molding with capability to disperse DEET in solution with the fragrance oil as a vapor into the atmosphere may be specifically formulated from the following components.

| Ingredient | Percent |
|---|---|
| Heliotropine | 5.6% |
| Cyclamen Aldehyde | 5.15% |
| Hydroxycitronellal | 3.03% |
| Phenyl Ethyl Alcohol | 2.24% |
| Linalool | 8.96% |
| Linalyl Acetate | 2.24% |
| Geraniol | 1.24% |
| Propylene Glycol | 1.24% |
| Aldehyde C-11 (Undecylenic) | 0.34% |
| Aldshyde C-12 (Lauric) | 0.56% |
| Citronellol | 7.84% |
| Phenyl Ethyl Acetate | 0.45% |
| Amyl Cinnamic Aldehyde | 12.32% |
| Benzyl Acetate | 7.20% |
| Terpineol Alpha | 10.08% |
| Terpinyl Acetate | 10.08% |
| Eugenol U.S.P. | 7.17% |
| Ethyl Vanillin @ 10.0% PG | 2.24% |

-continued

| Ingredient | Percent |
| --- | --- |
| Aldehyde C-12 (Lauric) @ 10.0% PG | 0.56% |
| Geranium Chinese | 3.36% |
| Benzoin Siam Resin IS @ 50.0% BB | 1.12% |
| Lilial | 4.00% |
| n-amyl Salycylate | 3.00% |
| Total | 100.00% |

The foregoing ingredients are used in the preferred embodiment of the invention. Variations may be made within the scope of the invention.

To form a solid DEET vapor emitting insect repellent in accordance with the invention, DEET is added to the above described liquid fragrance oil in concentrations dependent upon the final concentration of DEET desired in the final polymeric product. The concentration of DEET in the liquid system can be varied between 1% and approximately 20% by weight.

Another application for the mixture of a low-volatile material such as DEET and a suitably formulated fragrance is in the manufacture of insect repellent candles. The combination of the DEET and fragrance can be placed in a wax melt which is poured or pressed into a candle mold and then solidified. The resulting candle will repel insects when it is burned. The heat radiated by the burning of the candle warms the wax distant enough from the flame to avoid decomposition but near enough to experience increased molecular motion to release a vapor of the fragrance which carries the DEET and creates a repelling environment for flying insects. The repellent action of the DEET carried by the fragrance vapor released from the candles is many times more effective than citronella candles. The pressed candle repels flying insects, due to the action of the timed vapor release system, without being lit.

The ineffectiveness of citronella candles has been reported in the Journal of the American Mosquito Control Association, Vol. 12, No. 2, pp. 293–94 (1996), in an article entitled "Evaluation of the Efficacy of 3% Citronella Candles and 5% Citronella Incense for Protection Against Field Populations of Aedes Mosquitoes", Lindsay et al. The authors reported a study of the efficacy of commercially available citronella candles. Experiments were performed on live subjects. The authors concluded that "citronella candles . . . were ineffective for reducing the biting pressure of mosquitoes, and their use by the general public should be discouraged."

In the formation of a liquid airwick repellent system, either ethyl alcohol or a combination of ethyl alcohol and water can be added to the fragrance oil and DEET solution. The addition of water added to the system has the effect of retarding the rate of evaporation of the DEET vapor. For highest rates of evaporation, the liquid fragrance oil and DEET solution is mixed with ethyl or isopropyl alcohol and no water. The following percentages of DEET, fragrance oil, water and alcohol are preferred: DEET 10%, fragrance oil 5%; alcohol 59%; water 8%; and isopropyl palmitate, a surfactant, 18%. The surfactant is required to enable the DEET to mix with the water and alcohol base of the liquid which is vaporized in the airwick. The alcohol in the foregoing mixture may be varied in the range of 10% to 80% by weight whereas the amount of water can be between 5% and 30% by weight.

Water is added to the solution to decrease the evaporation rate of DEET vapor repellent while extending the life of the system. There is a limitation on the proportion of water that can be added in that only an amount of water which will allow for complete dissolving of all of the organic ingredients can be added. Since the organic ingredients, i.e., fragrance oil and DEET, are not soluble in water unless surfactants are used. The limiting factor is the solubility of the solution of DEET and the fragrance in the water and ethyl alcohol solution.

Unlike Citronella applicators, the towelette of the instant invention has a timed vapor release mechanism. In using prior art towlettes, one must apply the repellent to all exposed parts of the body, i.e., arms, neck, face, and legs. These prior art products depend on an insect approaching and coming in contact with the exposed area of an individual. Therefore, the individual must use the prior art product so as to cover all of the exposed skin.

With the towelette of the invention, one only need apply the towelette around the wrists and elbows if the concentration of flying insects is relatively low. The formulation allows the DEET vapor to escape to areas surrounding the body resulting in the repelling of flying insects. The percentage of the area of required coverage of the body depends upon the concentration of flying insects. In typical situations, one towlette can contain a sufficent amount of Deet repellent solution to be used to protect many people. The ability of several persons to share a single towelette enhances economy associated with the protection of groups of people.

The fragrance oil, which can include mineral oil, acts as both a moisturizer for the skin and a matrix that allows for the slow release of both the fragrance and DEET vapor.

The use of high-end ingredients for the fragrance allows for an extended release time of the DEET vapor to a point where the repellency is effective for up to 8 to 10 hours.

As can be seen in the following examples, the efficacy of the repellent system has been tested successfully throughout the world.

EXAMPLE 1

A study was done to assess, under field conditions, the efficacy of insect-repellent wristbands manufactured from the above solid forms of the insect repellent of the invention containing DEET in comparison with wrist bands containing Citronella, another common topically applied insect repellent. Similar results can be expected when the DEET and fragrance oil liquid system is mixed with alcohol or water and alcohol in an air-wick. The dispersion of the DEET vapor into the atmosphere is accomplished by evaporation of the fragrance oil similar to the way the DEET vapor is dispersed from a thermoplastic system.

The DEET wristbands contained as the active ingredient, 9.5% N,N-diethyl-m-toluamide. The Citronella wristbands contained as the active ingredient, 10% Citronella. Experiments were done to determine the comparative effectiveness of the DEET and Citronella based wristbands in protecting against bites from Aedes species mosquitoes. Further studies were made with 10% DEET containing 3% fragrance formulations and with 10 citronella with 3% fragrance as a contact repellent, i.e., placed on the surface of the circumference of a wrist.

The study of Example 1 was conducted in various countries in locations that contained large deciduous wood-lots with secondary growths under the canopy. Surrounding the regions in which the experiments were conducted were numerous pools which served as sources of Aedes species mosquitoes. Previous studies had shown that the selected sites are inhabited by sufficient numbers of adult mosquitoes for conducting evaluations of repellents.

Eight human subjects and a supervisor participated in the evaluation of each of the wristbands. Six of the subjects wore wrist bands on their arms and no other repellent. The other two of the subjects wore no wrist bands and no repellent of any kind. The subjects were selected at random from the population in each of the countries in which the experiments were conducted. Both male and female subjects weighing from 110 pounds to 230 pounds participated in the experiments. The subjects was dressed in identical green coveralls. Head nets and white cotton gloves were also worn by the subjects.

For each experiment, all eight of the subjects were uniformly spaced along the circumference of a circle with the distance between adjacent subjects being approximately 50 to 70 feet. During each experiment, The subjects were rotated about the circle so that each of the subjects was placed in each position twice, each time, for a duration of two minutes.

Biting accounts in which the number of bites experienced by each subject was counted were done each evening at dusk on each day of the experiments and consisted of twelve, two-minute counts of the number of bites experienced by each subject at each position. During the experiments, each of the subjects stood with his or her arms suspended without movement, their arms being exposed from wrist to elbow. During each two-minute period, the subjects aspirated all of the mosquitoes landing and probing on their two exposed forearms. After each biting count, the subjects recorded the number of mosquitoes captured and then rotated to the next position. The subjects rotated to each position twice per night. During the proposed study, each subject performed an equal number of two-minute biting counts at each of the six positions.

Ambient air temperature, relative humidity, and wind speed within the study site were measured during the course of each evening. Biting counts were not conducted if the air temperature was below 15 degrees Centigrade or when strong winds (greater or equal to 25 KMPH) or rain occurred because these conditions limit mosquito-host-seeking activity. If the biting fell below a minimum of one bite per minute per unprotected subject, i.e. subjects not earing a wristband, the trial was postponed until the following evening.

Table 1 shows the results of the experiments done to test the effectiveness of the wrist bands. During all of the times noted in Table 1, conditions were acceptable for testing each of the repellant products under the criteria set forth above.

TABLE 1

| Date | City | Total Time (Min.) | A | B | C(g) | D(g) | E |
|---|---|---|---|---|---|---|---|
| 4/22/96 | New Delhi, India | 24 | 3(a) | 8(a) | 2 | 0 | 35 |
| 4/24/96 | New Delhi, India | 24 | 6(c) | 10(b) | 4 | 0 | 42 |
| 4/28/96 | New Delhi, India | 24 | 9(e) | 18(c) | 3 | 0 | 48 |
|  | New Delhi, India | 24 | 14(f) | 24(d) | 2 | 0 | 52 |
| 7/9/96 | New Orleans, La. | 24 | 2(a) | 6(a) | 1 | 0 | 43 |
| 7/10/96 | New Orleans, La. | 24 | 5(b) | 9(b) | 2 | 0 | 38 |
| 7/12/96 | New Orleans, La. | 24 | 8(d) | 14(c) | 2 | 0 | 37 |
| 7/14/96 | New Orleans, La. | 24 | 10(f) | 18(d) | 2 | 0 | 32 |
| 7/2/96 | Hong Kong | 24 | 2(a) | 6(a) | 1 | 0 | 28 |
| 7/3/96 | Hong Kong | 24 | 5(b) | 8(b) | 1 | 0 | 31 |
| 7/4/96 | Hong Kong | 24 | 9(c) | 12(c) | 0 | 0 | 28 |
| 7/5/96 | Shenzhen, China | 24 | 3(a) | 6(a) | 1 | 0 | 31 |

TABLE 1-continued

| Date | City | Total Time (Min.) | A | B | C(g) | D(g) | E |
|---|---|---|---|---|---|---|---|
| 7/6/96 | Shenzhen, China | 24 | 5(b) | 9(b) | 2 | 0 | 33 |
| 7/7/96 | Shenzhen, China | 24 | 8(c) | 11(c) | 0 | 0 | 28 |
| 7/9/96 | Taipei, Taiwan | 24 | 4(a) | 7(a) | 1 | 0 | 33 |
| 7/11/96 | Seoul, Korea | 24 | 1(a) | 4(a) | 1 | 0 | 27 |
| 7/12/96 | Seoul, Korea | 24 | 3(b) | 6(b) | 2 | 0 | 24 |
| 7/13/96 | Tokyo, Japan | 24 | 1(a) | 3(a) | 1 | 0 | 37 |
| 7/14/96 | Tokyo, Japan | 24 | 2(b) | 6(b) | 1 | 0 | 33 |
| 7/29/96 | Guelph, Ontario | 24 | 1(a) | 2(a) | 0 | 0 | 35 |
| 7/30/96 | Guelph, Ontario | 24 | 3(b) | 5(b) | 1 | 0 | 38 |

A = Wristband with 10% DEET
B = Wristband with 10% Citronella
C = Liquid solution with 10% citronella plus 3% fragrance.
D = Liquid solution 10% DEET plus 3% fragrance.
E = No protection (average)
(a) = 3 hours on wrist at time of exposure.
(b) = 24 hours on wrist at time of exposure.
(c) = 48 hours on wrist at time of exposure.
(d) = 72 hours on wrist at time of exposure.
(e) = 96 hours on wrist at time of exposure
(f) = 120 hours on wrist at time of exposure.
(g) = Freshly applied prior to exposure.

As can be seen from Table 1, the temperatures in New Delhi, India ranged from 85 to 90 degrees Fahrenheit from Apr. 22, 1996 through Apr. 28, 1996. During that period, the humidity was approximately 50 percent. In New Orleans, the temperatures ranged from 88 to 93 degrees Fahrenheit and the humidity was approximately 90 percent. The temperature in Hong Kong ranged from 85 to 90 degrees Fahrenheit. The humidity in Hong Kong was in the range of 60 to 70 percent. In Shenzhen, China, the temperatures ranged from 95 to 98 degrees Fahrenheit. The humidity in Shenzhen was approximately 40 percent. Taipei, Taiwan and Seoul, Korea ranged in temperature from 80 to 85 degrees Fahrenheit with a humidity of approximately of 45 percent. In Tokyo, Japan, the temperatures ranged from 85 to 88 degrees Fahrenheit and the humidity was approximately 40 percent. In Guelph, Ontario, Canada, the temperatures ranged from 83 to 85 degrees Fahrenheit and the humidity was approximately 90 percent with rained occurring on one evening.

The results shown in Table 1 indicate that, in all cases, both wristbands performed effectively over a period of 120 hours as insect-repellants. However, the wristband containing DEET outperformed the wristband containing Citronella. A diminishment in performance over time was observed. This decrease in effectiveness was expected since the amount of vapor released from the band is reduced as function of time.

Both liquid formulations performed very well. However, the liquid formulation containing approximately 10 percent DEET outperformed the Citronella formulation. It is particularly significant that in each country, no mosquito bites were observed on any of the individuals using the liquid DEET liquid system. The fact that the liquid system was only placed around the circumference of the wrist confirmed that the fragrance carries DEET vapor molecules into the environment surrounding the exposed body to repel flying insects.

The volunteers who were not protected received the predicted bite counts in the areas in which the products were tested based on the number of mosquitoes in each test area. Measurable differences in bite count due to variations in weight of the subjects were not made in this study.

EXAMPLE 2

An assessment was made, under field conditions, of the ability of a DEET impregnated tablecloth and citronella impregnated tablecloth to reduce biting activity of aedes species mosquitoes. In the tests, a DEET impregnated tablecloth containing 9.5% n,n-diethyl-m-toluamide was used, as were a tablecloth containing approximately 10% citronella, and an untreated tablecloth, i.e., a tablecloth containing no insect repellent.

A second study was conducted in the same countries as in Example 1 during the same period of time. Like the wristband experiments of Example 1, the studies directed to tablecloths were conducted, to the extent feasible, in large deciduous wood-lots with secondary growths under the canopy. Surrounding the regions in which the experiments were conducted were numerous pools which served as sources of Aedes species mosquitoes. Previous studies had shown that the selected sites are inhabited by sufficient numbers of adult mosquitoes for conducting evaluations of repellents.

Nine subjects participated in the evaluation of each of the wristbands. The tests were carried out with the tablecloths positioned on three standard picnic tables, each having a table surface area measuring six by four feet supported three feet above the ground. One of the tables was covered with either an ordinary plastic tablecloth (i.e. the non-treated tablecloth. The other two tables were respectively covered with the two separate test tablecloths, one containing DEET and the other Citronella. The three tables were separated by at least fifteen feet and the tablecloths were placed onto the tables immediately prior to the start of each evaluation. Three positions at each table were designated and biting counts were performed at each location.

The subjects were randomly assigned to one of nine positions at the three tables. Biting accounts were initiated at dusk and consisted of twelve, two-minute biting counts. Each of the subjects sat with their arms suspended over the table but did not come into direct contact with the surface of the table cloth.

During each two-minute period, the subjects aspirated all mosquitoes landing and probing on two exposed forearms. After each biting count, the subjects recorded the number of mosquitoes captured and then rotated to the next position. Each of the subjects rotated and/or alternated among the tables covered with a tablecloth treated with DEET, a tablecloth treated with Citronella and a tablecloth which was untreated such that each subject occupied several positions per night.

During each evening of the study, each of the volunteers performed an equal number of two-minute biting counts at each of the tables. After the first evening the positions of the subjects at the tables were interchanged at random.

Ambient air temperature, relative humidity and wind speed within the study site were measured during the course of each evening. Biting counts were not conducted if the air temperature was below 15 degrees Centigrade (62 degrees Fahrenheit) or when strong winds, i.e., greater than or equal to 25 KMPH, or rain occurred because these conditions limit mosquito-host-seeking activity. If the biting activity fell below a minimum of one bite per minute per subject seated at a table with an untreated tablecloth, the trial was postponed until the following evening.

In addition to the above described steps, the tablecloths were left out on a continuous basis to determine their efficacy as insect repellents over a period of approximately 120 hours. Both treated tablecloths showed significant repellent effectiveness. However, in each instance, the DEET treated tablecloth outperformed the Citronella treated tablecloth in repelling insects.

Table 2 shows the results of the experiments done to test the effectiveness of the tablecloths. During all of the times noted in Table 2, conditions were acceptable for testing each of the repellant tablecloths under the criteria set forth above.

TABLE 2

| Date | City | Total Time (Min.) | A | B | C(g) |
|---|---|---|---|---|---|
| 4/22/96 | New Delhi, India | 24 | 0(a) | 3(a) | 38 |
| 4/24/96 | New Delhi, India | 24 | 2(c) | 5(b) | 46 |
| 4/26/96 | New Delhi, India | 24 | 4(e) | 8(c) | 49 |
| 4/28/96 | New Delhi, India | 24 | 4(f) | 10(d) | 58 |
| 7/9/96 | New Orleans, La. | 24 | 0(a) | 4(a) | 45 |
| 7/10/96 | New Orleans, La. | 24 | 0(b) | 6(b) | 41 |
| 7/12/96 | New Orleans, La. | 24 | 1(d) | 9(c) | 42 |
| 7/14/96 | New Orleans, La. | 24 | 3(f) | 12(d) | 38 |
| 7/2/96 | Hong Kong | 24 | 0(a) | 3(a) | 32 |
| 7/3/96 | Hong Kong | 24 | 2(b) | 6(b) | 29 |
| 7/4/96 | Hong Kong | 24 | 3(c) | 9(c) | 38 |
| 7/5/96 | Shenzhen, China | 24 | 0(a) | 2(a) | 33 |
| 7/6/96 | Shenzhen, China | 24 | 0(b) | 6(b) | 30 |
| 7/7/96 | Shenzhen, China | 24 | 2(c) | 8(c) | 38 |
| 7/9/96 | Taipei, Taiwan | 24 | 0(a) | 3(a) | 36 |
| 7/11/96 | Seoul, Korea | 24 | 0(a) | 3(a) | 31 |
| 7/12/96 | Seoul, Korea | 24 | 1(b) | 5(b) | 29 |
| 7/13/96 | Tokyo, Japan | 24 | 0(a) | 4(a) | 41 |
| 7/14/96 | Tokyo, Japan | 24 | 2(b) | 6(b) | 45 |

A = Tablecloth impregnated with 10% DEET
B = Tablecloth impregnated with 10% Citronella
C = Untreated Tablecloth
(a) = 3 hours of exposure to environment.
(b) = 24 hours of exposure to environment.
(c) = 48 hours of exposure to environment
(d) = 72 hours of exposure to environment.
(e) = 96 hours of exposure to environment
(f) = 120 hours of exposure to environment.

EXAMPLE 3

Four chromatograms were made to verify that the fragrance is a necessary vehicle for causing the DEET to be volatilized from a non-volatile matrix such as plastic. In order to facilitate the experiment, wax was used to simulate the thermoplastic material. Four samples were prepared and subjected to a head space analyzer.

Sample No. 1 consisted of wax with no fragrance or DEET and was the control to show that the wax, alone, gave off no emissions;

Sample No. 2 consisted of wax plus DEET added in an amount of 7.5% by weight and was the control to show that the DEET had no appreciable emission;

Sample No. 3 consisted of wax plus fragrance added in an amount of 7.5% by weight and was the control to show that the fragrance had no components in the area where DEET elutes; and Sample No. 4 consisted of wax plus DEET added in an amount of 7.5% by weight and fragrance added in an amount of 7.5% by weight for confirming that the DEET vapor is driven from the matrix by the fragrance.

In order to accelerate the test and attain results within a short time frame, the head space measurements were made at an elevated incubation temperature of 150° C. The experiments confirmed that the wax alone (Sample 1) gave off no emissions, wax plus DEET added in an amount of 7.5% by weight (Sample 2) also had no appreciable emission, wax plus fragrance added in an amount of 7.5% by weight (Sample 3) had no components in the area where DEET elutes, and wax plus DEET added in an amount of 7.5% by weight and fragrance added in an amount of 7.5% by weight (Sample 4) had substantial amounts of DEET, i.e., sufficient to repel insects, driven from the matrix by the fragrance.

EXAMPLE 4

A second set of experiments we done in an attempt to extract the fragrance and DEET, to extinction, from a thermoplastic material. A set of chromatograms representing successive extraction from a single pellet were made. The effectiveness of the fragrance in promoting the emission of DEET vapor from the plastic was demonstrated.

EXAMPLE 5

An further experiment was done to measure the effective life of insect repellent compositions consisting of DEET and fragrance mixed into a thermoplastic matrix.

Five grams of pellets consisting of DEET and fragrance mixed into a thermoplastic matrix were put into a cylinder capped at both ends and having gas fittings on the end caps. The inlet end was attached to a source of helium gas and a control valve. The outlet end was connected to a trap containing activated charcoal. The sample was purged for 1 hour at a rate of approximately 50 milliliters per minute. After an hour, the trap was replaced and purging was continued. The emissions captured in the trap were periodically extracted and analyzed for and DEET and fragrance content. Results showed that DEET vapor was released from the matrix with the fragrance in quantities sufficient to repel insects for 124 hours.

EXAMPLE 6

Single pellets weighing approximately 0.3 grams and consisting of DEET and fragrance mixed into a thermoplastic matrix were placed in a head space that contained inlet and outlet ports. From the inlet port, helium was introduced at a flow rate of 40–50 milliliters per minute. The outlet port was directly connected to a charcoal trap. Gas flow continued for 4–5 hours. The products that were trapped in the charcoal were extracted and analyzed in a Perkin Elmer vapor phase chromatograph containing capillary columns. It was observed that, at ambient temperatures, both the DEET and fragrance vaporized into the atmosphere.

EXAMPLE 7

The same experiment as reported in Example 5 above was done except without fragrance in the pellet. No significant amount of DEET was detected in the trapped products.

EXAMPLE 8

The same experiment as reported in Example 5 above was done except without DEET in the pellet. The fragrance was then detected in the products extracted from the charcoal filter.

EXAMPLE 9

A single pellet weighing approximately 0.3 grams and consisting of DEET and fragrance mixed into a thermoplastic matrix was heated to 150° C. and exhaustive extraction was carried out over a head space. The emissions were analyzed with a Perkin Elmer vapor phase chromatograph. The results showed that DEET vapor was emitted at a constant rate until the fragrance was completely vaporized from the pellet.

EXAMPLE 10

A single pellet of thermoplastic material weighing 0.3 grams and containing approximately 10% of DEET liquid was exposed to 150° C. and exhaustive extraction over the head space for 4–5 hours was done. No DEET was detected in the emissions when analyzed with the Perkin Elmer vapor phase chromatograph.

EXAMPLE 11

Approximately 0.3 grams of a single pellet of thermoplastic material containing approximately 10% fragrance was placed in a head space and heated to 150° C. Exhaustive extraction was carried our over 4–5 hours and all of the fragrance was detected using a Perkin Elmer vapor phase chromatograph.

Experiments carried out with wax and a combination of DEET and fragrance show that both DEET vapor and the fragrance are released into the environment on the burning of the candle.

EXAMPLE 12

A candle containing DEET without fragrance was burned. No DEET vapor was released.

EXAMPLE 13

A candle containing fragrance without DEET was burned. The fragrance was released from the candle.

EXAMPLE 14

A candle containing a specifically formulated fragrance and DEET was burned. The fragrance and DEET vapor were both released from the candle. As expected, there was an acceleration of the release of the fragrance and DEET vapor from the burning candle in comparison with release rates of DEET vapor and fragrance measured at ambient temperatures. The fragrance, as described above, drove the DEET from the matrix when the wax system was exposed to the heat given off by the flame of the lit candle. This resulted in DEET vapor being released into the atmosphere at much lower temperatures than the boiling point of DEET.

EXAMPLE 15

A study was done to assess, under laboratory conditions, the efficacy of candles impregnated with N, N-diiethyl-M-toluamide (Deet: concentration unknown) to repel laboratory-reared Aedis aegypti mosquitoes.

To determine the efficacy of deet-impregnated candles to repel mosquitoes, the number of mosquitoes moving within an inner and outer cage apparatus was determined in cages containing either no candle, a plain candle (lit and unlit) or a deet candle (lit and unlit).

The outer cage (35.5×37.0×38.5 cm) was screened on all sides except the front which was made of clear plexiglass with a sleeve located two-thirds from the top of the cage. The inner cage (25.5×25.7×26.2 cm) was made or clear plexiglass with a 12.8 cm hole on one side. Candles were lit, placed centrally into the inner cage and allowed to burn for one hour before mosquitoes were introduced. A 100 ml flask containing a 10 % glucose solution was placed between the candle and the back of the cage.

Approximately 100 mosquitoes (range 68–134) were placed into the outer cage onto the top of the inner cage. After one hour the candle was extinguished, the inner cage hole was sealed and the number of mosquitoes in both cages was determined. The percent repellency provided by the candles was determined by calculating the percentage of mosquitoes that entered the inner cage after one hour compared to the percentage entering the inner case In the control tests (no candle). These percentages were compared using the formula: [(percentage of mosquitoes entering inner cage with no candle−percentage of mosquitoes entering inner cage with candle)/percentage of mosquitoes entering inner cage with no candle]×100%. Each test was performed once and therefore statistical analysis was not performed.

The level of protection provided by the deet-impregnated candles is summarized in Tables 3 and 4. Fewer mosquitoes, relative to the control, entered the inner cage containing a lit deet candle (86.7%) or a lit plain candle (48.8%). When candles were present in the inner cage, but unlit, fewer mosquitoes, relative to the control, entered the inner cage containing the deet candle (72.5%) or the plain candle (5.7%).

TABLE 3

Percent repellency provided by burning deet-impregnated and plain candles against laboratory-reared *Aedis aegypti* mosquitoes

| Treatment | N | Number of Mosquitoes introduced[a] | Percentage in outer cage (%)[b] | Percentage in inner cage (%)[b] | Percentage reduction[c] |
| --- | --- | --- | --- | --- | --- |
| No Candle | 1 | 68 | 66.2 | 33.8 | NA[d] |
| Plain candle | 1 | 81 | 82.7 | 17.3 | 48.8 |
| Deet Candle | 1 | 134 | 95.5 | 4.5 | 86.7 |

[a]After candle burned for one hour.
[b]One hour after introduction of mosquitoes.
[c]Percent reduction calculated as: [(percentage or mosquitoes entering inner cage with no candle−percentage of mosquitoes entering inner cage with candle)/percentage or mosquitoes entering inner cage with no candle] × 100%
[d]not applicable

TABLE 4

Percent repellency provided by unlit deet-impregnated candles and plain candles against laboratory-reared *Aedis aegypti* mosquitoes

| Treatment | N | Number of mosquitoes introduced[a] | Percentage in outer cage (%)[b] | Percentage in inner cage (%)[b] | Percentage reduction[c] |
| --- | --- | --- | --- | --- | --- |
| No candle | 1 | 118 | 66.9 | 33.1 | NA[d] |
| Plain candle | 1 | 96 | 68.8 | 31.2 | 5.7 |
| Deet Candle | 1 | 133 | 91.0 | 9.0 | 72.8 |

[a]After candle present for one hour.
[b]One hour after introduction of mosquitoes.
[c]Percent reduction calculated as: [(percentage or mosquitoes entering inner cage with no candle−percentage of mosquitoes entering inner cage with candle)/percentage or mosquitoes entering inner cage with no candle] × 100%
[d]Not applicable As can be seen from the foregoing, the objects of the invention have been realized. Moreover, oral studies on rats and dogs with doses of the DEET liquid of the invention, of up to 300 mg/kg daily yielded no evidence of gross microscopic damage to any tissues and organs including blood, liver, kidney, spleen, pancreas and bone marrow. In 90-day subacute dermal studies on rabbits and on dogs at 300 mg/kg daily (liquid) no evidence of systemic toxicity was observed. Examination included all major tissues and organs.

Human subjects, patch tested with undiluted and with 50% compound solutions for a total of 23 applications each, showed no evidence of primary irritation or sensitization. Undiluted compound (liquid) applied to abraded skin of human subjects did not prolong the healing time.

Moreover, n,n-diethyl-m-toluamide does not produce teratogenic affects in pregnant rats after oral application (liquid) during the fifth through fifteenth day of pregnancy, even at concentrations greater than 90 mg/kg. In addition, clinical trials performed by the (U.S. Air Force have shown that the use of DEET can reduce the number of effective bites 15 times per hour compared to the use of no protection.

It is to be appreciated that the foregoing is a description of a preferred embodiments of the invention to which variations and modifications may be made without departing from the spirit and scope of the invention.

What is claimed is:

1. A candle for repelling flying insects comprising a body of wax material which has a melting point of not greater than 225 degrees F., and a liquid insect repellent imbedded in the wax material during molding of the candle, the liquid insect repellent including a mixture of DEET and a fragrance oil having volatile fragrance components and retentive components which prevent flash off of the fragrance components, the flash off temperature of the fragrance oil being greater than the melting point of the wax material, such that when the candle is lit, portions of the fragrance components are vaporized and carry with them portions of the DEET into the proximate atmosphere to repel flying insects.

2. A candle in accordance with claim 1 wherein the melting point of the wax material is no greater than 200° F.

3. A candle in accordance with claim 1 wherein the flash off temperature of the fragrance oil is no greater than 200° F.

4. A candle in accordance with claim 1 wherein the DEET is present in an amount of 1% to 20% by weight of the liquid insect repellent.

5. A method of making a candle for use in repelling flying insects before the insects can land on a surface in proximity to the candle comprising preparing a liquid insect repellent by mixing DEET with a fragrance oil having volatile fragrance components and retentive components which prevent flash off of the fragrance components, molding a mixture of candle wax, which has a melting point of not greater than 225 degrees F., and said liquid insect repellent at a temperature greater than the melting point of the candle wax and less than the flash off temperature of the fragrance components to embed the liquid insect repellent within the candle wax, such that when the candle is lit, portions of the fragrance components are vaporized and carry with them portions of the DEET into the proximate atmosphere to repel flying insects before they can land.

6. A method of making a candle in accordance with claim 5 wherein the candle is molded at a temperature of less than 200° F.

* * * * *